United States Patent
Kamiguchi (10) Patent No.: US 11,183,370 B2
(45) Date of Patent: Nov. 23, 2021

(54) CHARGED PARTICLE BEAM TREATMENT APPARATUS

(71) Applicant: SUMITOMO HEAVY INDUSTRIES, LTD., Tokyo (JP)

(72) Inventor: Nagaaki Kamiguchi, Tokyo (JP)

(73) Assignee: SUMITOMO HEAVY INDUSTRIES, LTD., Tokyo (JP)

( * ) Notice: Subject to any disclaimer, the term of this patent is extended or adjusted under 35 U.S.C. 154(b) by 55 days.

(21) Appl. No.: 16/824,307

(22) Filed: Mar. 19, 2020

(65) Prior Publication Data

US 2020/0303165 A1    Sep. 24, 2020

(30) Foreign Application Priority Data

Mar. 20, 2019    (JP) .............................. JP2019-052697

(51) Int. Cl.
| | | |
|---|---|---|
| *H01J 37/32* | (2006.01) | |
| *H01J 37/34* | (2006.01) | |
| *A61N 5/10* | (2006.01) | |

(52) U.S. Cl.
CPC ........ *H01J 37/3233* (2013.01); *A61N 5/1043* (2013.01); *A61N 5/1081* (2013.01); *H01J 37/3458* (2013.01); *A61N 2005/1055* (2013.01)

(58) Field of Classification Search
CPC .............. H01J 37/3458; H01J 37/3233; A61N 5/1045; A61N 5/1049; A61N 5/1067; A61N 5/1081; A61N 2005/1055; A61N 2005/1041; G01R 33/3806; G01R 33/4808

See application file for complete search history.

(56) References Cited

U.S. PATENT DOCUMENTS

| | | | | |
|---|---|---|---|---|
| 4,726,046 A | * | 2/1988 | Nunan ................. | A61N 5/1042 250/492.1 |
| 5,311,028 A | * | 5/1994 | Glavish ................. | H01F 3/02 250/492.21 |
| 8,880,250 B2 | | 11/2014 | Wu et al. | |
| 8,888,829 B2 | * | 11/2014 | Ward ................... | A61N 5/0624 606/10 |
| 9,475,403 B2 | | 10/2016 | Wu et al. | |
| 2006/0106301 A1 | * | 5/2006 | Kats ......................... | A61N 5/10 600/415 |
| 2010/0090123 A1 | * | 4/2010 | Tajiri ....................... | G21K 5/00 250/398 |

(Continued)

FOREIGN PATENT DOCUMENTS

WO    WO-2012/118589 A1    9/2012

*Primary Examiner* — Amy Cohen Johnson
*Assistant Examiner* — Syed M Kaiser
(74) *Attorney, Agent, or Firm* — Michael Best & Friedrich LLP (57) ABSTRACT

A charged particle beam treatment apparatus includes an irradiator that irradiates an irradiation target with a charged particle beam by a scanning method, in which the irradiator includes a scanning electromagnet that performs scanning with the charged particle beam, is rotatable around the irradiation target by a rotating gantry, and emits the charged particle beam with a base axis orthogonal to a center line of the rotating gantry and passing through the center line as a reference, and when the scanning electromagnet is not operated, the charged particle beam which is emitted from a tip portion of the irradiator is inclined in one direction with respect to the base axis.

3 Claims, 8 Drawing Sheets

(56) References Cited

U.S. PATENT DOCUMENTS

| | | | |
|---|---|---|---|
| 2010/0239066 A1* | 9/2010 | Fahrig | A61N 5/1049 378/65 |
| 2012/0165652 A1* | 6/2012 | Dempsey | A61B 90/37 600/411 |
| 2013/0035584 A1* | 2/2013 | Fahrig | A61N 5/1083 600/411 |
| 2015/0217136 A1* | 8/2015 | Stanescu | A61B 5/055 600/411 |
| 2015/0273240 A1* | 10/2015 | Balakin | A61N 5/1081 250/396 ML |
| 2016/0136461 A1* | 5/2016 | Iwata | A61N 5/1079 600/1 |
| 2017/0340900 A1* | 11/2017 | Moore | G16H 50/50 |
| 2017/0372867 A1* | 12/2017 | Caspi | A61N 5/1081 |
| 2018/0099158 A1* | 4/2018 | Brusasco | G01R 33/4215 |
| 2018/0180693 A1* | 6/2018 | Boernert | A61N 5/1049 |
| 2019/0274649 A1* | 9/2019 | Fahrig | A61N 5/1049 |
| 2020/0147412 A1* | 5/2020 | Ni | A61N 5/1049 |
| 2020/0261745 A1* | 8/2020 | Shimakura | A61N 5/103 |
| 2020/0303165 A1* | 9/2020 | Kamiguchi | A61N 5/1043 |

\* cited by examiner

CHARGED PARTICLE BEAM TREATMENT APPARATUS

RELATED APPLICATIONS

The content of Japanese Patent Application No. 2019-052697, on the basis of which priority benefits are claimed in an accompanying application data sheet, is in its entirety incorporated herein by reference.

BACKGROUND

Technical Field

Certain embodiments of the present invention relate to a charged particle beam treatment apparatus.

Description of Related Art

In the related art, as a charged particle beam treatment apparatus for performing treatment by irradiating an affected part of a patient with a charged particle beam, for example, an apparatus described in the related art is known. In the charged particle beam treatment apparatus according to the related art, a charged particle beam accelerated by an accelerator is emitted from an irradiator by a scanning method. That is, the irradiator performs irradiation while moving an irradiation position of the charged particle beam to the affected part by performing scanning with a scanning electromagnet.

SUMMARY

According to an embodiment of the present invention, there is provided a charged particle beam treatment apparatus including an irradiator that irradiates an irradiation target with a charged particle beam by a scanning method, in which the irradiator includes a scanning electromagnet that performs scanning with the charged particle beam, is rotatable around the irradiation target by a rotating gantry, and emits the charged particle beam with a base axis orthogonal to a center line of the rotating gantry and passing through the center line as a reference, and when the scanning electromagnet is not operated, the charged particle beam which is emitted from a tip portion of the irradiator is inclined in one direction with respect to the base axis.

DETAILED DESCRIPTION

Here, in a case of performing the irradiation in the scanning method as described above, a controller causes an electric current to flow through the scanning electromagnet in both positive and negative directions to shift a magnetic field of the scanning electromagnet to both poles, whereby the charged particle beam performs scanning to both sides with respect to a base axis. However, in a region where the electric current flowing through the scanning electromagnet is close to zero, a proportional relationship between an electric current and a voltage is broken, and therefore, there is a case where the scanning with the charged particle beam is not stable. In this case, there is a problem in that the accuracy of the irradiation position of the charged particle beam is affected.

It is desirable to provide a charged particle beam treatment apparatus in which it is possible to stabilize scanning with a charged particle beam.

In the charged particle beam treatment apparatus, when the scanning electromagnet is not operated, the charged particle beam which is emitted from the tip portion of the irradiator is inclined in one direction with respect to the base axis. In this case, by causing a predetermined magnitude of electric current to flow through the scanning electromagnet in one direction, it is possible to emit the charged particle beam along the base axis. Further, by adjusting the magnitude of the electric current with the electric current at this time as a reference, it is possible to perform the scanning with the charged particle beam in one direction and the opposite direction with respect to the base axis. In this manner, it is possible to perform the scanning with the charged particle beam by adjusting the electric current in a range of a certain magnitude or more. That is, since it is possible to perform the scanning with the charged particle beam without using a region in the vicinity of a region where the electric current becomes zero, it is possible to stabilize the scanning with the charged particle beam.

The charged particle beam treatment apparatus may further include a transporter that transports the charged particle beam to the irradiator, and the transporter may change a trajectory of the charged particle beam in a predetermined plane to cause the charged particle beam to be incident on the irradiator, and when the scanning electromagnet is not operated, the charged particle beam which is emitted from the tip portion of the irradiator may be inclined with respect to the base axis when viewed at least in a direction orthogonal to the plane. In this case, by adjusting the trajectory of the charged particle beam in the transporter, it is possible to easily adjust the inclination of the charged particle beam which is emitted from the tip portion of the irradiator with respect to the base axis.

The charged particle beam treatment apparatus may further include a bending electromagnet that changes a trajectory of the charged particle beam, and the scanning electromagnet may be disposed on the downstream side of the bending electromagnet. The inclination of the charged particle beam with respect to the base axis can be adjusted by shortening the bending electromagnet. In this manner, it is possible to achieve downsizing of the entire rotating gantry by shortening the bending electromagnet which is a heavy object.

According to the present invention, it is possible to provide a charged particle beam treatment apparatus in which it is possible to stabilize scanning with a charged particle beam.

Hereinafter, a charged particle beam treatment apparatus according to an embodiment of the present invention will be described with reference to the accompanying drawings. In the description of the drawings, the same elements will be denoted by the same reference numerals, and overlapping description will be omitted.

Figure 1:
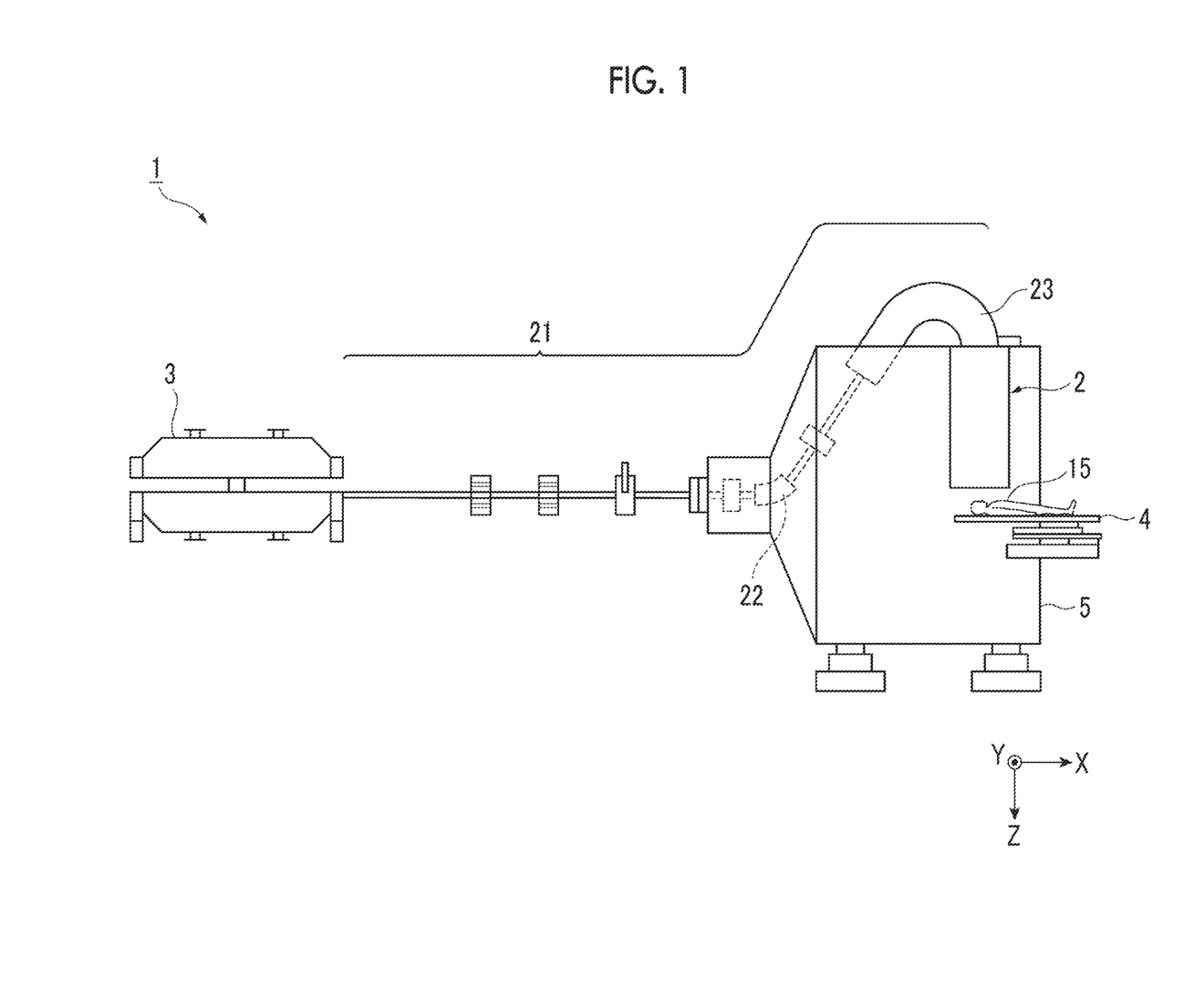
FIG. 1 is a schematic configuration diagram showing a charged particle beam treatment apparatus according to an embodiment of the present invention.

FIG. 1 is a schematic configuration diagram showing a charged particle beam treatment apparatus 1 according to an embodiment of the present invention. The charged particle beam treatment apparatus 1 is an apparatus which is used for cancer treatment or the like by radiation therapy. The charged particle beam treatment apparatus 1 includes an accelerator 3 that accelerates charged particles generated in an ion source device and emits the charged particles as a charged particle beam, an irradiator 2 that irradiates an irradiation target with the charged particle beam, and a beam transport line 21 (a transporter) for transporting the charged particle beam emitted from the accelerator 3 to the irradiator 2.

The irradiator 2 is mounted to a rotating gantry 5 provided so as to surround a treatment table 4. The irradiator 2 is made to be rotatable around the treatment table 4 by the rotating gantry 5. The beam transport line 21 enters the rotating gantry 5 from the rear end side of the rotating gantry 5. Then, the beam transport line 21 changes the trajectory of the charged particle beam to the outer periphery side by a bending electromagnet 22, then greatly bends the trajectory of the charged particle beam by a bending electromagnet 23, and enters the irradiator 2 from the outer periphery side.

Figure 2:
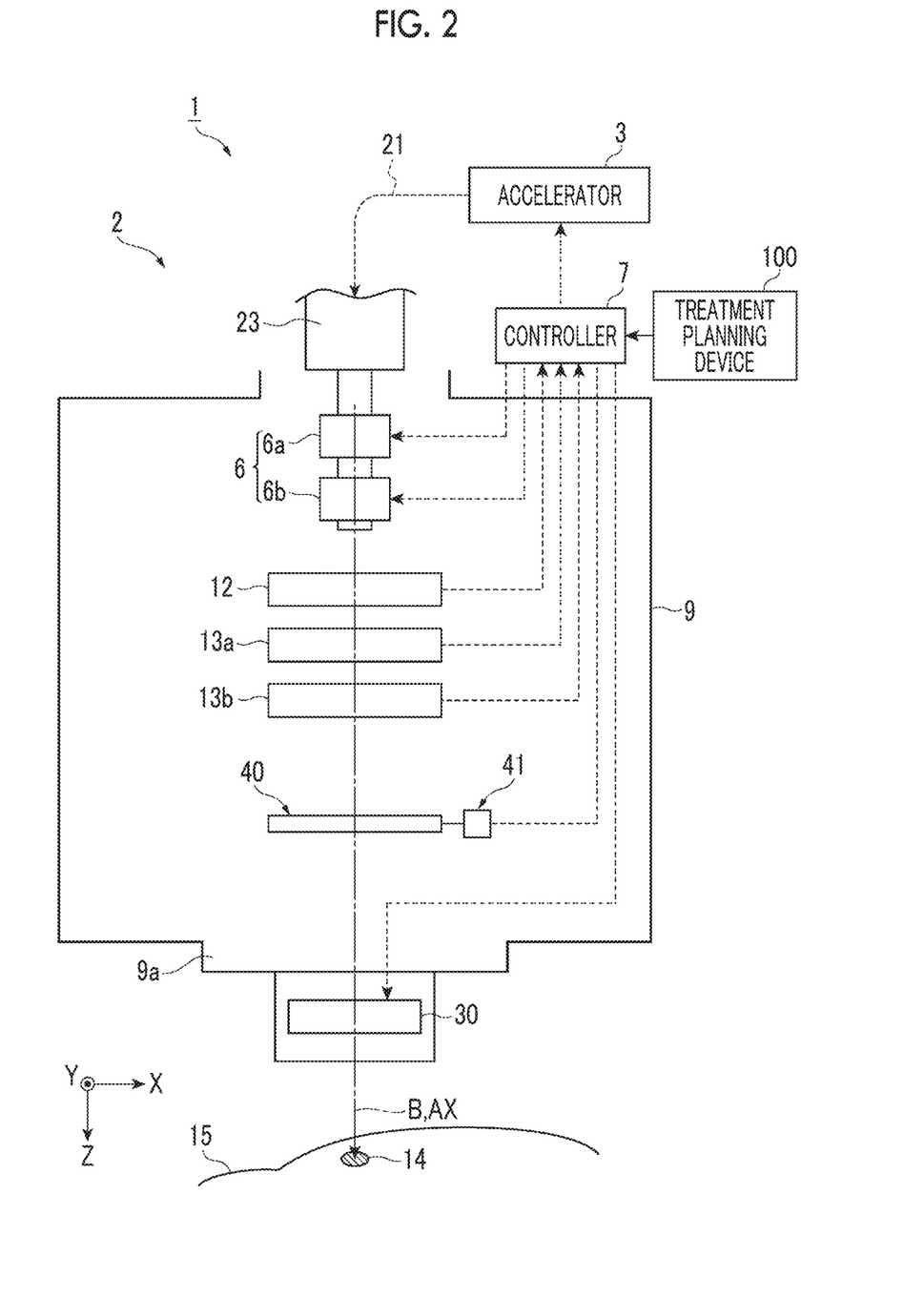
FIG. 2 is a schematic configuration diagram of the vicinity of an irradiator of the charged particle beam treatment apparatus of FIG. 1.

FIG. 2 is a schematic configuration diagram of the vicinity of the irradiator of the charged particle beam treatment apparatus of FIG. 1. In the following description, description will be made using the terms "X-axis direction", "Y-axis direction", and "Z-axis direction". The "Z-axis direction" is a direction along a base axis AX of the irradiator 2 and is an irradiation depth direction of a charged particle beam B. The details of the "base axis AX" will be described later. FIG. 2 shows a state where the charged particle beam B is emitted along the base axis AX. The "X-axis direction" is one direction in a plane orthogonal to the Z-axis direction. The "Y-axis direction" is a direction orthogonal to the X-axis direction in the plane orthogonal to the Z-axis direction.

First, a schematic configuration of the charged particle beam treatment apparatus 1 according to this embodiment will be described with reference to FIG. 2. The charged particle beam treatment apparatus 1 is an irradiation apparatus according to a scanning method. The scanning method is not particularly limited, and line scanning, raster scanning, spot scanning, or the like may be adopted. As shown in FIG. 2, the charged particle beam treatment apparatus 1 includes the accelerator 3, the irradiator 2, the beam transport line 21, and a controller 7.

The accelerator 3 is a device that accelerates charged particles and emits the charged particle beam B having an energy set in advance. As the accelerator 3, a cyclotron, a synchrocyclotron, a linac, or the like can be given as an example. In a case where a cyclotron that emits the charged particle beam B having an energy determined in advance is adopted as the accelerator 3, it is possible to adjust (lower) the energy of the charged particle beam which is sent to the irradiator 2, by adopting an energy adjustment unit 20 (refer to FIG. 1). The accelerator 3 is connected to the controller 7, so that an electric current which is supplied thereto is controlled. The charged particle beam B generated by the accelerator 3 is transported to the irradiator 2 by the beam transport line 21. The beam transport line 21 connects the accelerator 3, the energy adjustment unit 20, and the irradiator 2, and transports the charged particle beam emitted from the accelerator 3 to the irradiator 2.

The irradiator 2 irradiates a tumor (an irradiation target) 14 in the body of a patient 15 with the charged particle beam B. The charged particle beam B is obtained by accelerating charged particles at a high speed, and a proton beam, a heavy particle (heavy ion) beam, an electron beam, or the like can be given as an example. Specifically, the irradiator 2 is a device that irradiates the tumor 14 with the charged particle beam B emitted from the accelerator 3 that accelerates the charged particles generated in an ion source (not shown) and transported by the beam transport line 21. The irradiator 2 includes a scanning electromagnet 6, a dose monitor 12, position monitors 13a and 13b, a collimator 40, and a degrader 30. The scanning electromagnet 6, the respective monitors 12, 13a, and 13b, and the degrader 30 are accommodated in an irradiation nozzle 9 as an accommodation body. In this manner, the irradiator 2 is configured by accommodating each main component in the irradiation nozzle 9. In addition to the elements described above, a quadrupole electromagnet and a profile monitor may be provided on the upstream side of the scanning electromagnet 6. Further, the dose monitor 12, the position monitors 13a and 13b, and the degrader 30 may be omitted.

The scanning electromagnet 6 includes an X-axis direction scanning electromagnet 6a and a Y-axis direction scanning electromagnet 6b. The X-axis direction scanning electromagnet 6a and the Y-axis direction scanning electromagnet 6b are each composed of a pair of electromagnets, change the magnetic field between the pair of electromagnets according to an electric current which is supplied from the controller 7, and perform scanning with the charged particle beam B which passes between the electromagnets. The X-axis direction scanning electromagnet 6a performs the scanning with the charged particle beam B in the X-axis direction, and the Y-axis direction scanning electromagnet 6b performs the scanning with the charged particle beam B in the Y-axis direction. The scanning electromagnets 6a and 6b are disposed in this order downstream of the charged particle beam B with respect to the accelerator 3 on the base axis AX. The scanning electromagnet 6 performs the scanning with the charged particle beam B such that the charged particle beam B is emitted on a scanning path planned in advance by a treatment planning device 100.

The dose monitor 12 is disposed on the downstream side of the scanning electromagnet 6 on the base axis AX. The position monitors 13a and 13b detect and monitor the beam shape and position of the charged particle beam B. The position monitors 13a and 13b are disposed downstream of the charged particle beam B with respect to the dose monitor 12 on the base axis AX. Each of the monitors 12, 13a, and 13b outputs the detected detection result to the controller 7.

The degrader 30 performs fine adjustment of the energy of the charged particle beam B by lowering the energy of the charged particle beam B passing therethrough. In this embodiment, the degrader 30 is provided at a tip portion 9a of the irradiation nozzle 9. The tip portion 9a of the irradiation nozzle 9 is an end portion downstream of the charged particle beam B.

The collimator 40 is a member that is provided downstream of the charged particle beam B with respect to at least the scanning electromagnet 6, blocks a part of the charged particle beam B, and passes a part of the charged particle beam B therethrough. Here, the collimator 40 is provided on the downstream side of the position monitors 13a and 13b. The collimator 40 is connected to a collimator driving unit 41 that moves the collimator 40.

The controller 7 includes, for example, a CPU, a ROM, a RAM, and the like. The controller 7 controls the accelerator 3, the scanning electromagnet 6, and the collimator driving unit 41, based on the detection results output from the respective monitors 12, 13a, and 13b.

Further, the controller 7 of the charged particle beam treatment apparatus 1 is connected to the treatment planning device 100 for performing a treatment plan of the charged particle beam treatment. The treatment planning device 100 measures the tumor 14 of the patient 15 by CT or the like before treatment, and plans a dose distribution (a dose distribution of the charged particle beam for irradiation) at each position of the tumor 14. Specifically, the treatment planning device 100 creates a treatment plan map with respect to the tumor 14. The treatment planning device 100 transmits the created treatment plan map to the controller 7. In the treatment plan map created by the treatment planning device 100, a scanning path to be drawn by the charged particle beam B is planned.

In a case of performing the irradiation with the charged particle beam by the scanning method, the tumor 14 is virtually divided into a plurality of layers in the Z-axis direction, and is irradiated by performing scanning with the charged particle beam in one layer so as to follow the scanning path defined in the treatment plan. Then, after the irradiation of the one layer with the charged particle beam is completed, the irradiation of the next adjacent layer with the charged particle beam B is performed.

In a case of performing the irradiation with the charged particle beam by the scanning method, first, the charged particle beam B is emitted from the accelerator 3. The emitted charged particle beam B performs scanning so as to follow the scanning path defined in the treatment plan by the control of the scanning electromagnet 6. In this way, the tumor 14 is irradiated while being scanned with the charged particle beam B within an irradiation range in one layer set in the Z-axis direction. When the irradiation with respect to one layer is completed, the next layer is irradiated with the charged particle beam B.

Figure 3A:
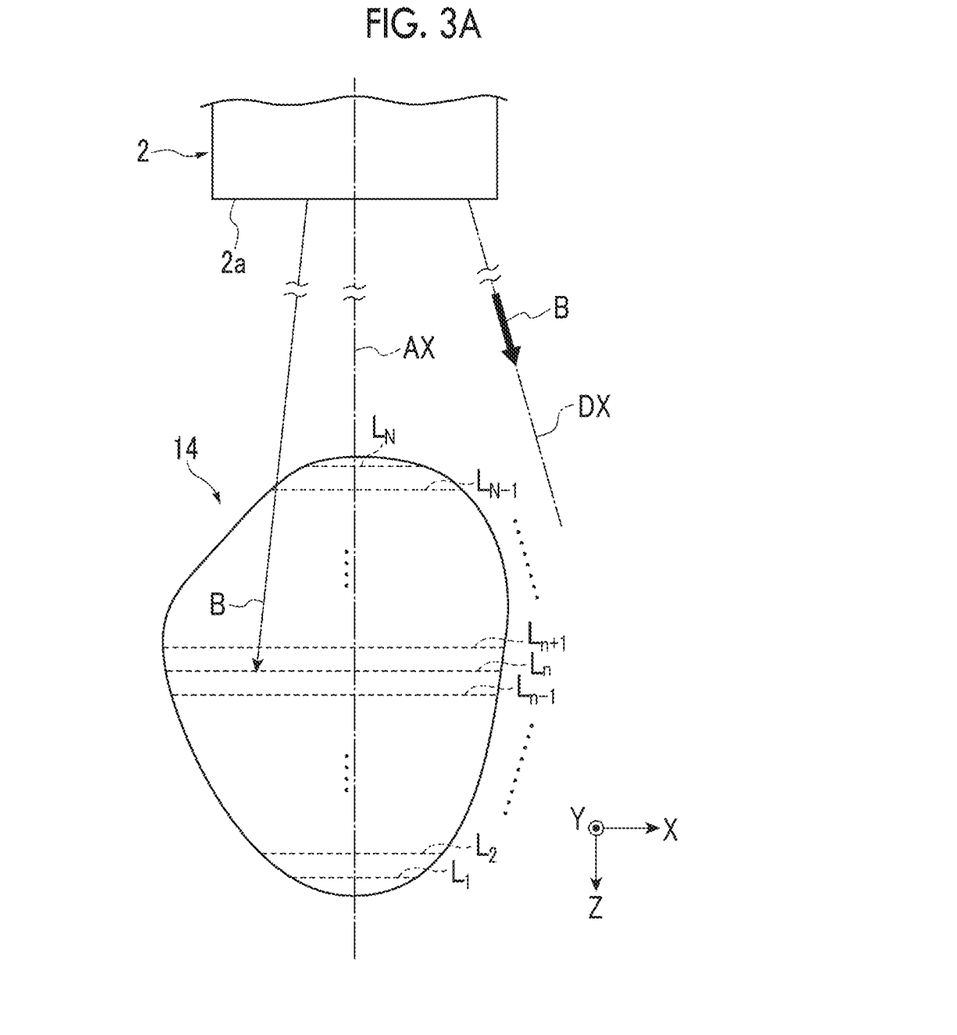
FIGS. 3A and 3B are diagrams showing layers set with respect to a tumor.
Figure 3B:
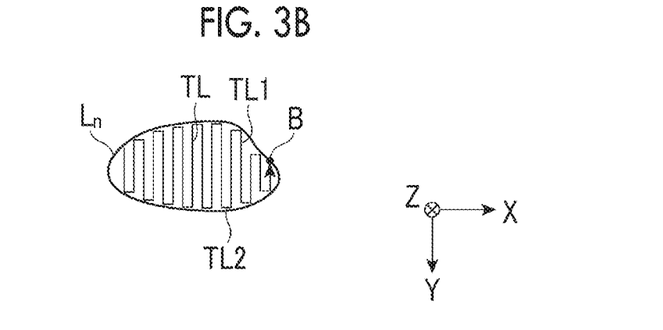

A charged particle beam irradiation image of the scanning electromagnet 6 under the control of the controller 7 will be described with reference to FIGS. 3A and 3B. FIG. 3A shows an irradiation target virtually sliced into a plurality of layers in a depth direction, and FIG. 3B shows a scanning image with the charged particle beam in one layer viewed in the depth direction.

As shown in FIG. 3A, the irradiation target is virtually sliced into a plurality of layers in the irradiation depth direction, and in this example, the irradiation target is virtually sliced into a layer L1, a layer L2, . . . , a layer Ln−1, a layer Ln, a layer Ln+1, . . . , a layer LN−1, a layer LN, and an N-th layer in order from a deep layer (a layer where the range of the charged particle beam B is long). Further, as shown in FIG. 3B, in the case of continuous irradiation (line scanning or raster scanning), the charged particle beam B performs continuous irradiation along a scanning path TL on the layer Ln while drawing a beam trajectory along the scanning path TL, and in the case of spot scanning, a plurality of irradiation spots on the layer Ln are irradiated with the charged particle beam B. The charged particle beam B performs irradiation along a scanning path TL1 extending in the X-axis direction, is shifted in the Y-axis direction along a scanning path TL2, and performs irradiation along the adjacent scanning path TL1. In this manner, the charged particle beam B emitted from the irradiator 2 controlled by the controller 7 moves on the scanning path TL.

Next, a detailed configuration of the charged particle beam treatment apparatus 1 according to this embodiment will be described.

Figure 6A:
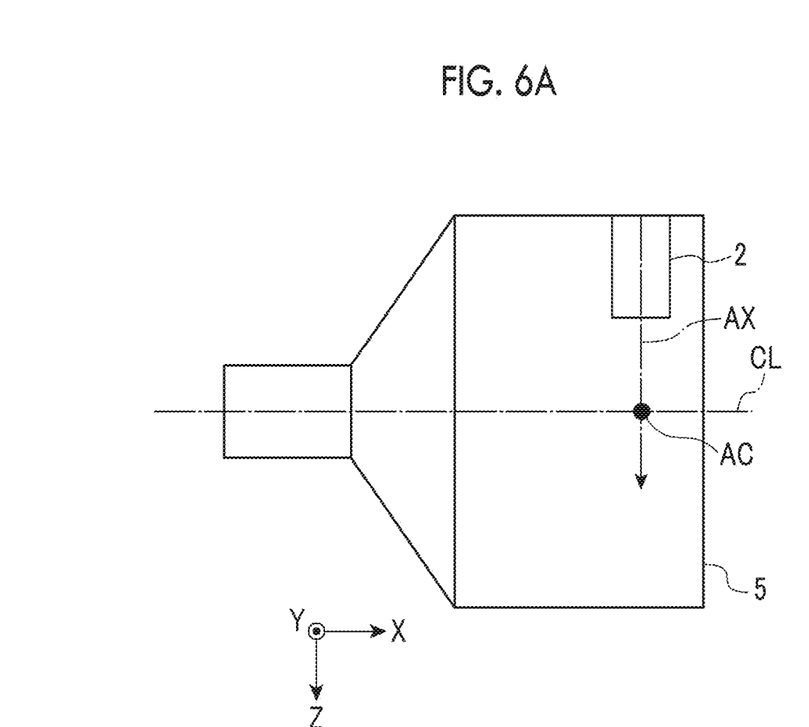
FIGS. 6A and 6B are schematic diagrams for describing a base axis of the irradiator.
Figure 6B:
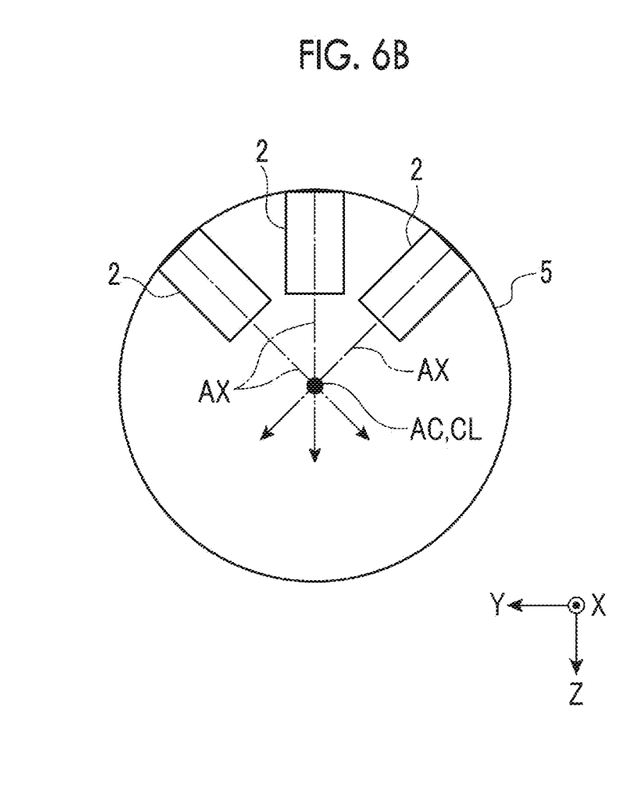

First, the "base axis AX" of the irradiator 2 will be described with reference to FIGS. 6A and 6B. The base axis AX is a virtual reference line serving as a reference when the irradiator 2 performs the irradiation with the charged particle beam B. Also when a scanning pattern is created when the treatment planning device 100 performs a treatment plan, the treatment plan is performed with the base axis AX as a reference. For example, in a case of setting the layers shown in FIG. 3A, each layer is assumed to be a plane perpendicular to the base axis AX. Also when setting the amount of movement in the X-axis direction and the amount of movement in the Y-axis direction, the position of the base axis AX is used as a reference. As shown in FIG. 6A, the base axis AX is orthogonal to a center line CL of the rotating gantry 5 and passes through the center line CL. The base axis AX passes through an isocenter AC on the center line CL of the rotating gantry 5. As shown in FIG. 6B, in a case where the irradiator 2 is rotated around the isocenter AC with the rotation of the rotating gantry 5, the base axis AX passes through the isocenter AC on the rotating gantry 5 regardless of the position of the irradiator 2.

Figure 4A:
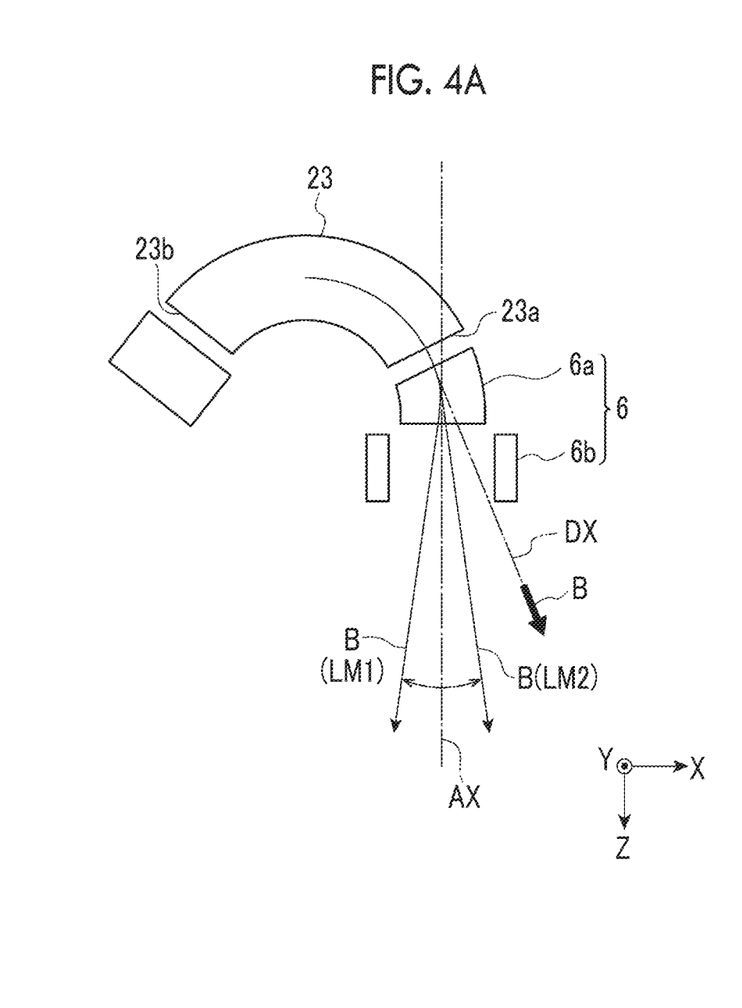
FIG. 4A shows an irradiation mode of a charged particle beam in the charged particle beam treatment apparatus according to the embodiment.
Figure 4B:
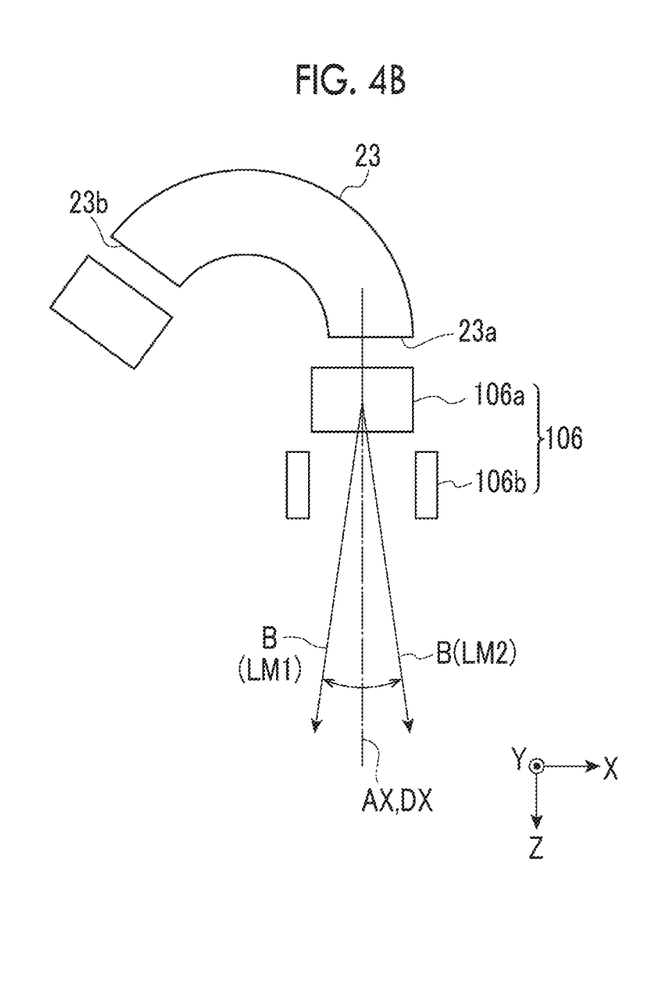
FIG. 4B shows an irradiation mode of a charged particle beam in a charged particle beam treatment apparatus according to a comparative example.

Next, a direction in which the charged particle beam B is emitted will be described with reference to FIGS. 4A and 4B. FIG. 4A shows an irradiation mode of the charged particle beam B in the charged particle beam treatment apparatus 1 according to this embodiment, and FIG. 4B shows an irradiation mode of the charged particle beam B in a charged particle beam treatment apparatus according to a comparative example. In the following description, description will be made in comparison with the configuration according to the comparative example as necessary.

A reference axis extending in a direction in which the charged particle beam B is emitted when the scanning electromagnet 6 is not operated is defined as an irradiation axis DX. A state where the scanning electromagnet 6 is not operated is a state where the electric current flowing through the scanning electromagnet 6 is zero, that is, a state where no electric current flows through the scanning electromagnet 6. In this case, even if the charged particle beam B is incident on the scanning electromagnet 6, the charged particle beam B directly passes through the scanning electromagnet 6 without changing the directions thereof in the X-axis direction and the Y-axis direction. As shown in FIG. 4A, the irradiation axis DX is inclined to one side (the positive side in the X-axis direction) with respect to the base axis AX of the irradiator 2. In this way, when the scanning electromagnet 6 is not operated, the charged particle beam B which is emitted from the scanning electromagnet 6 is inclined in one direction with respect to the base axis AX. As a result, when the scanning electromagnet 6 is not operated, the charged particle beam B which is emitted from a tip portion 2a of the irradiator 2 is inclined in one direction with respect to the base axis AX (refer to FIG. 3A).

The magnitude of the inclination of the irradiation axis DX with respect to the base axis AX is not particularly limited. However, the magnitude of the inclination may be set to, for example, a magnitude in a range in which the irradiation axis DX does not interfere with the Y-axis direction scanning electromagnet 6*b* on the downstream side. Alternatively, the magnitude of the inclination may be set to a magnitude in a range in which the charged particle beam B is emitted from the tip portion 2*a* of the irradiator 2 without interference of the irradiation axis DX with a member on the downstream side of the scanning electromagnet 6 (FIG. 3A). However, at this time, the collimator 40 is widened most greatly.

Such an inclination of the irradiation axis DX with respect to the base axis AX is formed by adjusting an emission angle from the bending electromagnet 23. The bending electromagnet 23 bends the trajectory of the charged particle beam B incident from an end portion 23*b* on the upstream side so as to draw an arc with a constant diameter, and emits the charged particle beam B from an end portion 23*a* on the downstream side. The bending electromagnet 23 is curved so as to draw an arc with a constant diameter. Here, in the comparative example shown in FIG. 4B, the bending electromagnet 23 emits the charged particle beam B along the base axis AX toward a scanning electromagnet 106. At this time, the emission-side end portion 23*a* of the bending electromagnet 23 is perpendicular to the base axis AX. In this way, the irradiation axis DX and the base axis AX coincided with each other.

In contrast, in this embodiment, as shown in FIG. 4A, the bending electromagnet 23 emits the charged particle beam B in a direction inclined with respect to the base axis AX. At this time, the emission-side end portion 23*a* of the bending electromagnet 23 is inclined with respect to the base axis AX. The end portion 23*a* is inclined toward the negative side in the Z-axis direction as it goes toward the positive side in the X-axis direction. In a case where the position of the upstream-side end portion 23*b* of the bending electromagnet 23 is the same between this embodiment of FIG. 4A and the comparative example of FIG. 4B, the downstream-side end portion 23*a* of the bending electromagnet 23 of this embodiment of FIG. 4A has a configuration in which it is interrupted before reaching the downstream-side end portion 23*a* of the comparative example of FIG. 4B. Therefore, the circumferential length of the bending electromagnet 23 of this embodiment of FIG. 4A is shorter than that of the bending electromagnet 23 according to the comparative example of FIG. 4B.

The bending electromagnet 23 changes the trajectory of the charged particle beam B in a plane extending in the XZ axis direction to cause the charged particle beam B to be incident on the irradiator 2. The bending electromagnet 23 described above can adjust the direction of the irradiation axis DX with respect to the base axis AX within the plane. Therefore, when the scanning electromagnet 6 is not operated, the charged particle beam B which is emitted from the scanning electromagnet 6 and the charged particle beam B which is emitted from the tip portion 2*a* of the irradiator 2 are inclined with respect to the base axis AX when viewed at least in a direction orthogonal to the plane extending in the XZ axis direction (here, the Y-axis direction).

Figure 5A:
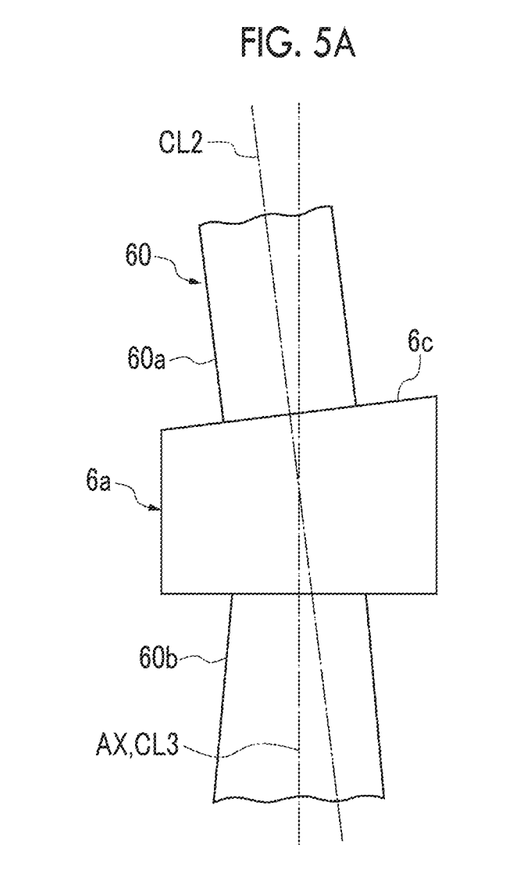
FIG. 5A is a diagram showing a configuration in the vicinity of a scanning electromagnet of the charged particle beam treatment apparatus according to the embodiment.
Figure 5B:
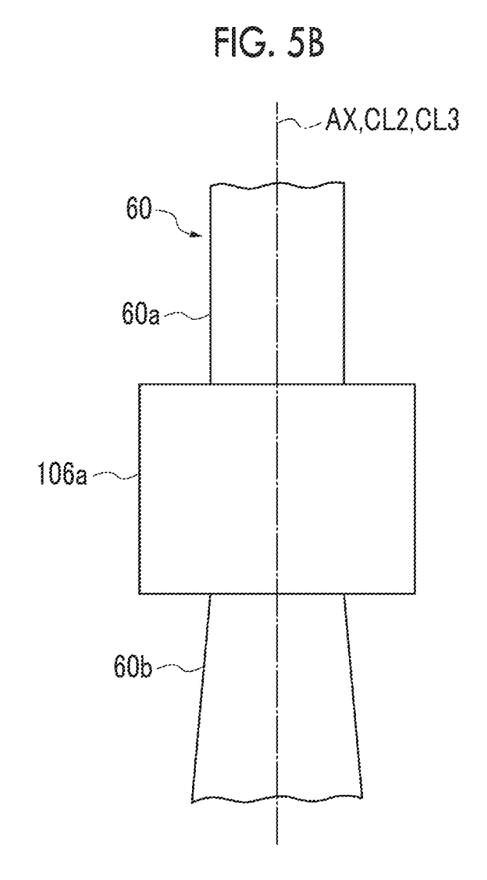
FIG. 5B is a diagram showing a configuration in the vicinity of a scanning electromagnet of the charged particle beam treatment apparatus according to the comparative example.

The configuration in the vicinity of the X-axis direction scanning electromagnet 6*a* will be described with reference to FIGS. 5A and 5B. The charged particle beam B passes through the X-axis direction scanning electromagnet 6*a* while moving inside a vacuum duct 60. As shown in FIG. 5B, in the comparative example, a center line CL2 of an upstream-side portion 60*a* of the duct 60 and a center line CL3 of a downstream-side portion 60*b* of the duct coincide with the base axis AX. On the other hand, as shown in FIG. 5A, in this embodiment, the center line CL3 of the downstream-side portion 60*b* of the duct 60 coincides with the base axis AX, whereas the center line CL2 of the upstream-side portion 60*a* of the duct 60 is inclined with respect to the base axis AX. An upstream-side end portion 6*c* of the X-axis direction scanning electromagnet 6*a* of this embodiment may be inclined with respect to the base axis AX by being inclined so as to be perpendicular to the center line CL2.

Figure 7:
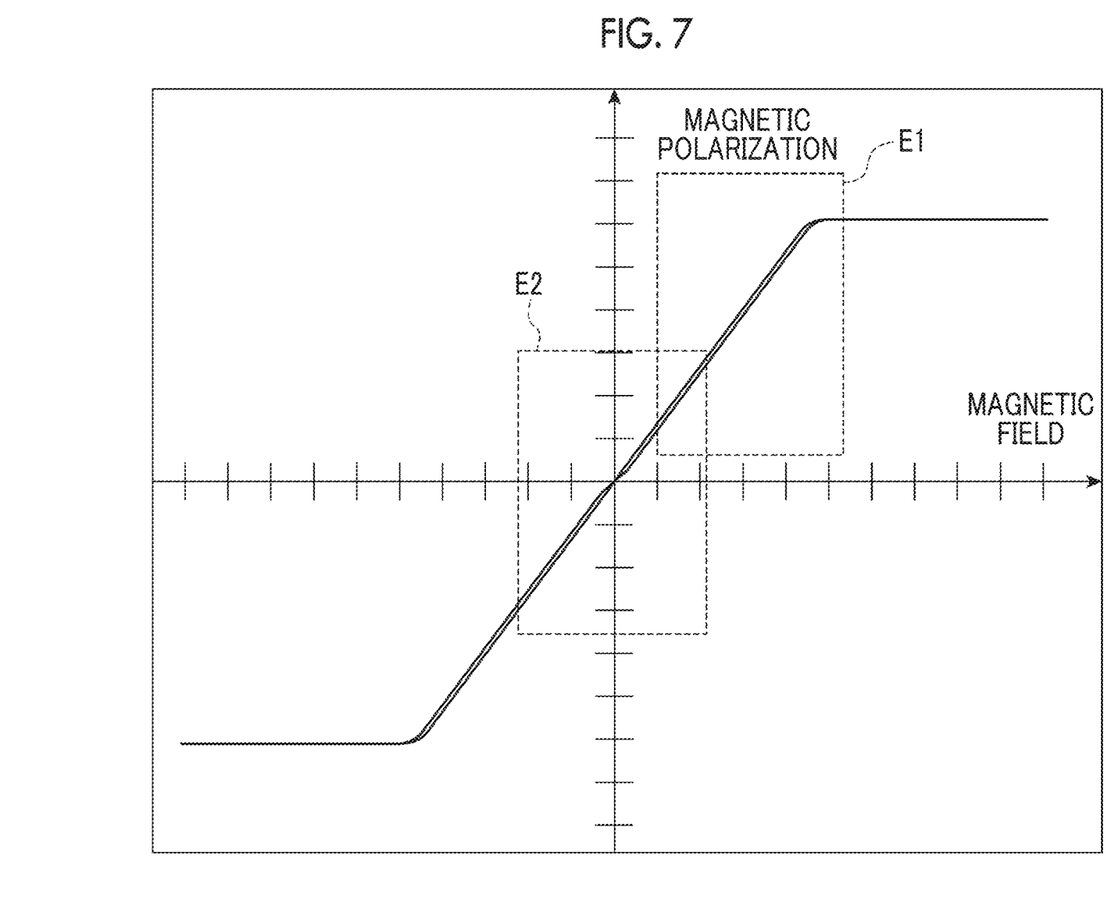
FIG. 7 is a graph showing a relationship between a magnetic field and magnetic polarization of the scanning electromagnet.

Next, a control mode of the scanning electromagnet 6 will be described with reference to FIGS. 4A, 4B, and 7. FIG. 7 is a graph showing a relationship between a magnetic field and magnetic polarization of the scanning electromagnet. When an electric current is applied to one side of the scanning electromagnet, the magnetic field is shifted to the positive side, and when an electric current is applied to the opposite side of the scanning electromagnet, the magnetic field is shifted to the negative side.

In the comparative example, a region indicated by E2 in FIG. 7 is used, and thus the direction of the magnetic field is shifted to both poles. As shown in FIG. 4B, when the controller 7 causes an electric current to flow to one side of the scanning electromagnet 106 to shift the magnetic field to the positive side, the charged particle beam B performs scanning to the negative side in the X-axis direction. When the controller 7 causes an electric current to flow to the other side of the scanning electromagnet 106 to shift the magnetic field to the negative side, the charged particle beam B performs scanning to the positive side in the X-axis direction. When the controller 7 applies the maximum magnetic field on the positive side in the range of E2 in FIG. 7, the charged particle beam B is shifted to a negative-side boundary position LM1 in the X-axis direction. When the controller 7 applies the maximum magnetic field on the negative side in the range of E2 in FIG. 7, the charged particle beam B is shifted to a positive-side boundary position LM2 in the X-axis direction.

In contrast, in this embodiment, a region indicated by E1 in FIG. 7 is used, and thus the direction of the magnetic field is shifted in only one direction. Further, in this embodiment, a region with a stronger magnetic field as compared with the comparative example is used. As shown in FIG. 4A, when the controller 7 causes an electric current to flow to one side of the scanning electromagnet 6 to shift the magnetic field to the positive side, the charged particle beam B performs scanning from the position of the irradiation axis DX to the negative side in the X-axis direction. That is, the charged particle beam B is shifted in a direction coming closer to the base axis AX than when no electric current is flowing through the scanning electromagnet 6. When the controller 7 causes a predetermined magnitude of electric current (a reference electric current) to flow through the scanning electromagnet 6, the charged particle beam B is emitted along the base axis AX. Then, the controller 7 adjusts the strength and weakness of the magnetic field by adjusting the magnitude of the electric current with the electric current at the base axis AX as a reference, whereby the charged particle beam B performs scanning to both sides. That is, the controller 7 causes an electric current larger than the reference electric current to flow through the scanning electromagnet 6, whereby it is possible to shift the charged particle beam B to the negative side in the X-axis direction from the base axis AX. When the controller 7 applies the maximum magnetic field in the range of E1 in FIG. 7, the charged particle beam B is shifted to the negative-side boundary position LM1 in the X-axis direction. The controller 7 causes an electric current smaller than the reference electric current to flow through the scanning electromagnet 6, whereby it is possible to shift the charged particle beam B to the positive side in the X-axis direction from the base axis AX. When the controller 7 applies the minimum magnetic field in the range of E1 in FIG. 7, the charged particle beam B is shifted to the positive-side boundary position LM2 in the X-axis direction. In order to perform such control, it is sufficient if the inclination of the irradiation axis DX with respect to the base axis AX is larger than the inclination of the negative-side boundary position LM2 in the X-axis direction of the scanning range with respect to the base axis AX.

In FIGS. 4A and 4B, the case where the irradiation axis DX of the X-axis direction scanning electromagnet 6a is inclined has been described. In addition to or instead of this, the irradiation axis DX of the Y-axis direction scanning electromagnet 6b may be inclined with respect to the base axis AX. In this case, the irradiation axis DX of the Y-axis direction scanning electromagnet 6b cannot be inclined only by adjustment of the emission direction of the bending electromagnet 23, and therefore, an electromagnet that deflects the direction of the charged particle beam B in the Y-axis direction is required on the upstream side of the Y-axis direction scanning electromagnet 6b.

Next, the operation and effects of the charged particle beam treatment apparatus 1 according to this embodiment will be described.

In the charged particle beam treatment apparatus 1, when the scanning electromagnet 6 is not operated, the charged particle beam B which is emitted from the tip portion 2a of the irradiator 2 is inclined in one direction (to the positive side in the X-axis direction) with respect to the base axis AX. In this case, a predetermined magnitude of electric current flows to the scanning electromagnet 6 in one direction, whereby the charged particle beam B can be emitted along the base axis AX. Further, by adjusting the magnitude of the electric current with the electric current at this time as a reference, it is possible to perform scanning with the charged particle beam B in one direction and the opposite direction with respect to the base axis AX. In this manner, it is possible to perform the scanning with the charged particle beam B by adjusting the electric current in a range of a certain magnitude or more. That is, since it is possible to perform the scanning with the charged particle beam B without using a region in the vicinity of the region where the electric current becomes zero, it is possible to stabilize the scanning with the charged particle beam B.

Further, according to the configuration described above, the scanning electromagnet 6 also functions as a bending electromagnet for transporting the charged particle beam B to the isocenter AC, and is always in an excited state. Since the scanning electromagnet 6 can be used as a part of a beam line, it is possible to achieve the downsizing of the rotating gantry 5. Further, since a somewhat strong magnetic field is used and a region that is almost saturated is used, magnetic permeability is low, inductance can be reduced, and a high-speed response becomes possible. That is, a portion having a low magnetic permeability is used, and therefore, the inductance can be reduced and an excitation speed can be increased. It is preferable that a scanning range has a magnetic pole length to the extent that does not cause zero cross. Further, since scanning can be performed using an electric current in one direction, it becomes possible to use a unipolar power source even without using an expensive bipolar power source as in the related art. In this way, the power source can be made inexpensive and small.

The charged particle beam treatment apparatus 1 includes the beam transport line 21 for transporting the charged particle beam B to the irradiator 2, the beam transport line 21 changes the trajectory of the charged particle beam B within a predetermined plane to cause the charged particle beam B to be incident on the irradiator 2, and when the scanning electromagnet 6 is not operated, the charged particle beam B which is emitted from the tip portion 2a of the irradiator 2 is inclined with respect to the base axis AX when viewed at least in a direction orthogonal to the plane. In this case, by adjusting the trajectory of the charged particle beam B in the beam transport line 21, it is possible to easily adjust the inclination of the charged particle beam B which is emitted from the tip portion 2a of the irradiator 2 with respect to the base axis AX.

The charged particle beam treatment apparatus 1 may include the bending electromagnet 23 that changes the trajectory of the charged particle beam B, and the scanning electromagnet 6 may be disposed on the downstream side of the bending electromagnet 23. The inclination of the charged particle beam B with respect to the base axis AX can be adjusted by shortening the bending electromagnet 23. In this manner, it is possible to achieve downsizing of the entire rotating gantry 5 by shortening the bending electromagnet 23 which is a heavy object.

The present invention is not limited to the embodiment described above.

Figure 8:
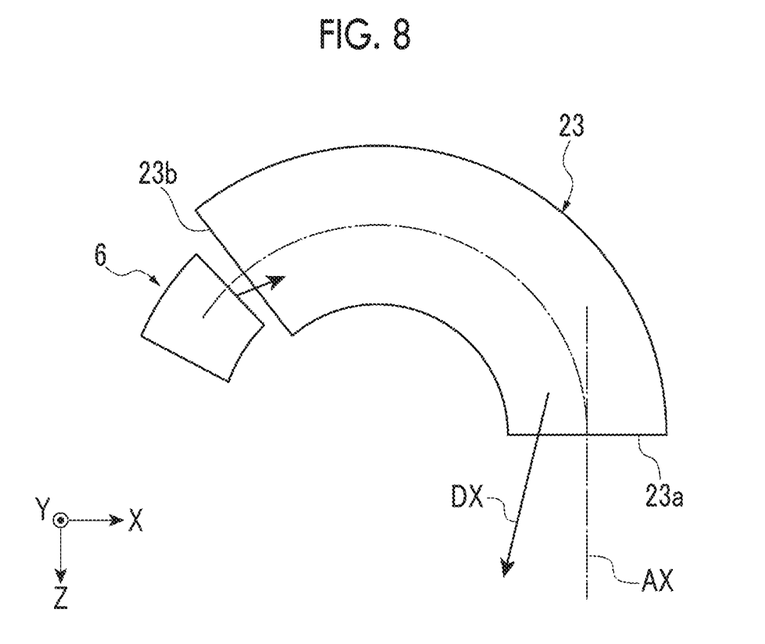
FIG. 8 is a diagram showing a configuration in the vicinity of a bending electromagnet of a charged particle beam treatment apparatus according to a modification example.

For example, the configuration shown in FIG. 8 may be adopted. The charged particle beam treatment apparatus shown in FIG. 8 includes the bending electromagnet 23 that changes the trajectory of the charged particle beam B, and the scanning electromagnet 6 is disposed on the upstream side of the bending electromagnet 23. In this case, since the distance from the scanning electromagnet 6 to the tip of the irradiator 2 becomes long, even when the scanning amount of the scanning electromagnet 6 is small, it is possible to obtain a sufficient scanning amount at the time of emission from the irradiator 2. In this way, it is possible to achieve the downsizing of the scanning electromagnet 6.

The charged particle beam treatment apparatus may include a bending electromagnet that changes the trajectory of the charged particle beam, and the scanning electromagnet may be disposed on the upstream side of the bending electromagnet. In this case, since the distance from the scanning electromagnet to the tip of the irradiator becomes long, even if the scanning amount of the scanning electromagnet is small, it is possible to obtain a sufficient scanning amount at the time of emission from the irradiator. In this way, downsizing of the scanning electromagnet can be achieved. Further, by adopting a structure in which the irradiation axis of the charged particle beam when the scanning electromagnet is not operated is inclined with respect to the base axis, it is possible to make the size of the entire bending electromagnet small.

It should be understood that the invention is not limited to the above-described embodiment, but may be modified into various forms on the basis of the spirit of the invention. Additionally, the modifications are included in the scope of the invention.

What is claimed is:

1. A charged particle beam treatment apparatus comprising:
   an irradiator that irradiates an irradiation target with a charged particle beam by a scanning method, wherein the irradiator
includes a scanning electromagnet that performs scanning with the charged particle beam,
is rotatable around the irradiation target by a rotating gantry, and
emits the charged particle beam with a base axis orthogonal to a center line of the rotating gantry and passing through the center line as a reference, and
when the scanning electromagnet is not operated, the charged particle beam which is emitted from a tip portion of the irradiator is inclined in one direction with respect to the base axis.

2. The charged particle beam treatment apparatus according to claim 1, further comprising:
a transporter that transports the charged particle beam to the irradiator,
wherein the transporter changes a trajectory of the charged particle beam within a predetermined plane to cause the charged particle beam to be incident on the irradiator, and
when the scanning electromagnet is not operated, the charged particle beam which is emitted from the tip portion of the irradiator is inclined with respect to the base axis when viewed at least in a direction orthogonal to the plane.

3. The charged particle beam treatment apparatus according to claim 1, further comprising:
a bending electromagnet that changes a trajectory of the charged particle beam,
wherein the scanning electromagnet is disposed on a downstream side of the bending electromagnet.

* * * * *